(12) United States Patent
Lin et al.

(10) Patent No.: US 11,723,546 B2
(45) Date of Patent: Aug. 15, 2023

(54) OPTICAL SENSING DEVICE

(71) Applicant: Wistron Corporation, New Taipei (TW)

(72) Inventors: Yi-Shang Lin, New Taipei (TW); Chih-Chen Chang, New Taipei (TW)

(73) Assignee: Wistron Corporation, New Taipei (TW)

( * ) Notice: Subject to any disclaimer, the term of this patent is extended or adjusted under 35 U.S.C. 154(b) by 384 days.

(21) Appl. No.: 16/914,444

(22) Filed: Jun. 28, 2020

(65) Prior Publication Data

US 2021/0275044 A1 Sep. 9, 2021

(30) Foreign Application Priority Data

Mar. 5, 2020 (TW) ................. 109107230

(51) Int. Cl.
| | |
|---|---|
| *A61B 5/026* | (2006.01) |
| *G01C 9/02* | (2006.01) |
| *A61B 5/00* | (2006.01) |
| *A61B 5/0205* | (2006.01) |
| *A61B 5/021* | (2006.01) |
| *A61B 5/145* | (2006.01) |

(52) U.S. Cl.
CPC .......... *A61B 5/0261* (2013.01); *A61B 5/0205* (2013.01); *A61B 5/684* (2013.01); *A61B 5/742* (2013.01); *G01C 9/02* (2013.01); *A61B 5/0077* (2013.01); *A61B 5/021* (2013.01); *A61B 5/14542* (2013.01); *A61B 2560/0475* (2013.01); *A61B 2562/185* (2013.01)

(58) Field of Classification Search
CPC ..... A61B 5/0261; A61B 5/0205; A61B 5/684; A61B 5/742; A61B 5/0077; A61B 5/021; A61B 5/14542; A61B 2560/0475; A61B 2562/185; A61B 5/6801; G01C 9/02
See application file for complete search history.

(56) References Cited

U.S. PATENT DOCUMENTS

| | | | |
|---|---|---|---|
| 2012/0259230 A1* | 10/2012 | Riley | A61B 5/445 600/477 |
| 2014/0275885 A1* | 9/2014 | Isaacson | A61B 5/14552 600/323 |
| 2017/0345274 A1* | 11/2017 | Chang | A61B 5/7405 |
| 2019/0108686 A1* | 4/2019 | Spivack | G06Q 30/0277 |
| 2019/0290176 A1* | 9/2019 | Vu | A61B 5/02416 |
| 2021/0236011 A1* | 8/2021 | Tarassenko | A61B 5/02125 |

FOREIGN PATENT DOCUMENTS

| | | |
|---|---|---|
| TW | 201803521 A | 2/2018 |
| TW | 201825045 A | 7/2018 |
| TW | 202001281 A | 1/2020 |

\* cited by examiner

*Primary Examiner* — Eric F Winakur
*Assistant Examiner* — Abid A Mustansir
(74) *Attorney, Agent, or Firm* — Winston Hsu

(57) ABSTRACT

An optical sensing device includes a device casing and an optical sensor on the device casing. In an embodiment, the optical sensing device further includes an image-capturing device on the device casing. The sensing direction of the optical sensor and the capturing direction of the image-capturing device point in the same direction. The image-capturing device can capture an image of an object to be sensed by the optical sensor. In another embodiment, the optical sensing device further includes a flexible shielding cover on the device casing and enclosing the optical sensor for shielding the optical sensor from external light.

10 Claims, 7 Drawing Sheets

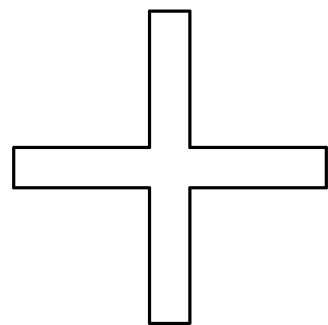
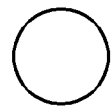
FIG. 5  FIG. 6
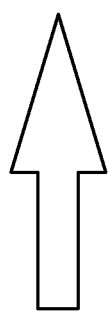
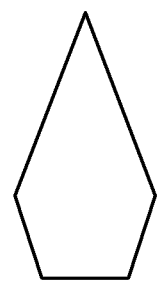
FIG. 7  FIG. 8

| | | |
|---|---|---|
| identification code | F0125 | ...... |
| sensing time | 20191205/16:35 | ...... |
| blood oxygen saturation(%) | 98 | ...... |
| systolic blood pressure(mmHg) | 105 | ...... |
| diastolic blood pressure(mmHg) | 75 | ...... |
| blood flow magnitude(ml/min) | 1100 | ...... |
| signal acquisition duration(sec) | 60 | ...... |
| image | 201912051635.jpg | ...... |
| level status(degree) | +5 | ...... |
| equipment number | AX0321 | ...... |
| firmware version | PPGSA0321.a2 | ...... |
| remarks | covered with cling film | ...... |

FIG. 10

OPTICAL SENSING DEVICE

BACKGROUND OF THE INVENTION

1. Field of the Invention

The present disclosure relates to an optical sensing device, and more particularly to an optical sensing device suitable for sensing physiological parameters.

2. Description of the Prior Art

There are currently applications for sensing physiological parameters using optical sensing, for example sensing pulse, blood flow, and the like by a photoplethysmography (PPG) technology. Its optical sensor usually emits light by itself and senses the light. Therefore, when there is interference from external light, it will affect the accuracy of the sensing. At present, there are optical sensing devices on the market for sensing the status of an arteriovenous fistula. The device body thereof is provided with an exposed optical sensor and a circular soft pad enclosing the optical sensor. When in use, the optical sensor is directed toward the patient's arteriovenous fistula and the device body is moved so that the optical sensor can be as close as possible to the arteriovenous fistula and the circular soft pad is as close as possible to the skin to prevent ambient light from entering the inside of the circular soft pad and interfering with the sensing of the optical sensor. However, the circular soft pad is usually sheet-like (or thin-plate-shaped) and has a limited amount of elastic deformation, and the surface morphology of the skin is usually not flat, which makes it difficult for the circular soft pad to completely closely fit with the skin. Besides, an actual arteriovenous fistula is usually uneven, which makes the surface morphology of the skin more uneven, leading to a very limited shielding effect of the circular soft pad. As a result, the optical sensor is likely to receive ambient light during sensing, which may make the sensing invalid or makes the reference value for the sensing low. Besides, an actual arteriovenous fistula usually deforms and increases in curvature as times by. The light-shielding function of the circular soft pad may totally fail, which makes the implement of the sensing of the optical sensing device difficult, or makes the sensing fail and the sensing value meaningless. Besides, the aforementioned deformation and curvature increase also make it difficult for the optical sensing device to perform sensing at the same location for a long period of time to observe changes in the arteriovenous fistula. Furthermore, sensing values obtained at different positions of the arteriovenous fistula or under different level statuses of the optical sensing device will be different. Current optical sensing devices only display or record sensing values, which cannot distinguish the sensing values based on the sensing posture (such as the aforementioned sensing position, the level status of the device during sensing, and so on) and makes the simple sensing values low for future reference.

SUMMARY OF THE INVENTION

An optical sensing device according to the disclosure includes a device casing, an optical sensor, and an image-capturing device. The optical sensor is disposed on the device casing and has a sensing direction. The optical sensor performs sensing in the sensing direction. The image-capturing device is disposed on the device casing and has a capturing direction. The sensing direction and the capturing direction point in the same direction. Thereby, the optical sensing device can use the image-capturing device to capture an image of an object to be sensed by the optical sensor.

Another optical sensing device according to the disclosure includes a device casing, an optical sensor, and a flexible shielding cover. The optical sensor is disposed on the device casing. The flexible shielding cover is disposed on the device casing and encloses the optical sensor. Thereby, the flexible shielding cover can conform to the surface morphology of an object to be sensed so as to completely closely fit with the object, so that the flexible shielding cover can provide the optical sensor sufficient light shielding effect.

These and other objectives of the present invention will no doubt become obvious to those of ordinary skill in the art after reading the following detailed description of the preferred embodiment that is illustrated in the various figures and drawings.

BRIEF DESCRIPTION OF THE DRAWINGS

FIG. 5 is a schematic diagram illustrating that an indication mark projected by a light source of the optical sensing device is a cross.

FIG. 6 is a schematic diagram illustrating that the indication mark is a circle.

FIG. 7 is a schematic diagram illustrating that the indication mark is an arrow.

FIG. 8 is a schematic diagram illustrating that the indication mark is a polygon.

FIG. 10 is a schematic diagram illustrating a format and an example of content recorded by a controller of the optical sensing device.

DETAILED DESCRIPTION

Figure 1:
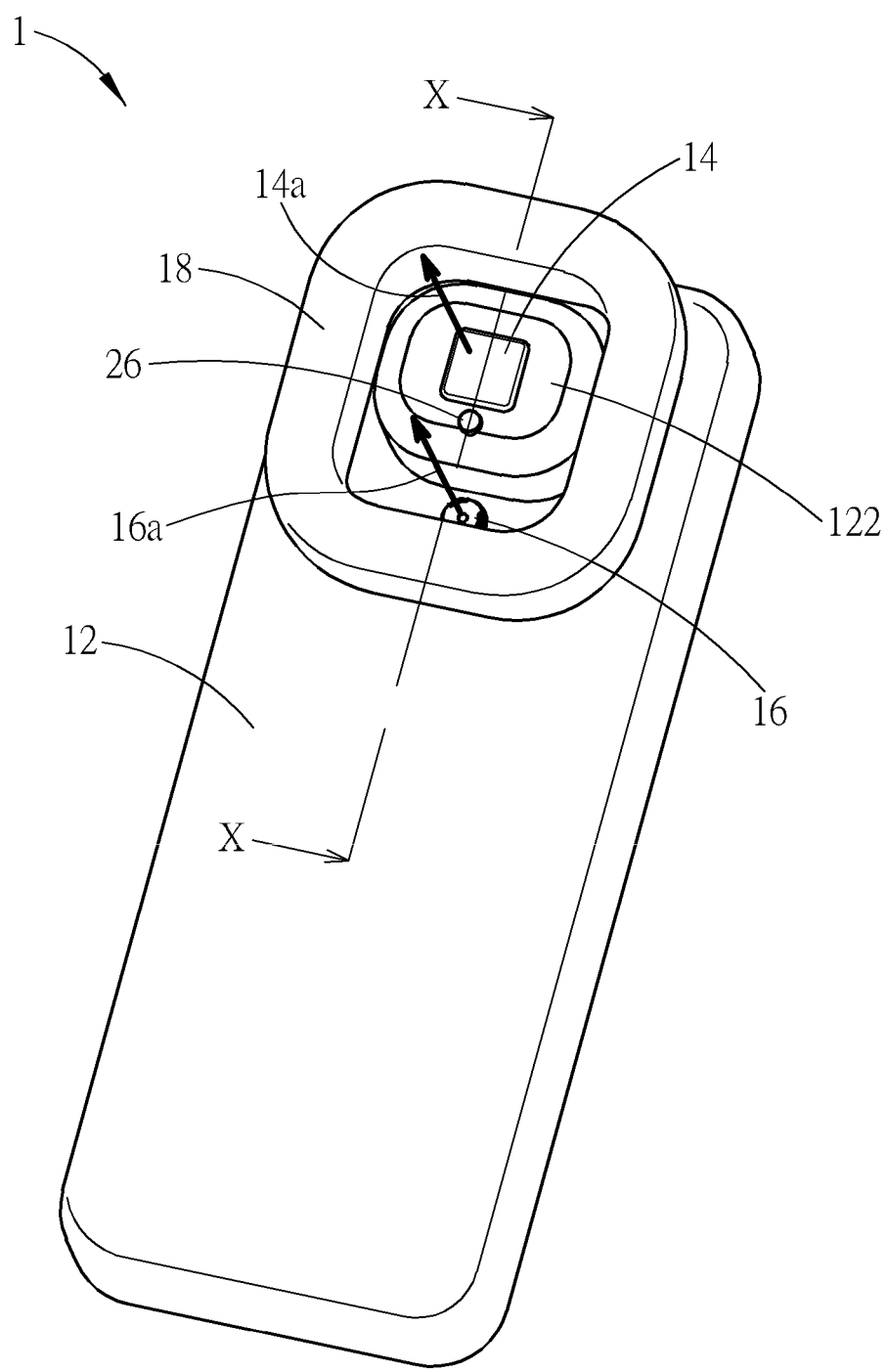
FIG. 1 is a schematic diagram illustrating an optical sensing device according to an embodiment.
Figure 2:
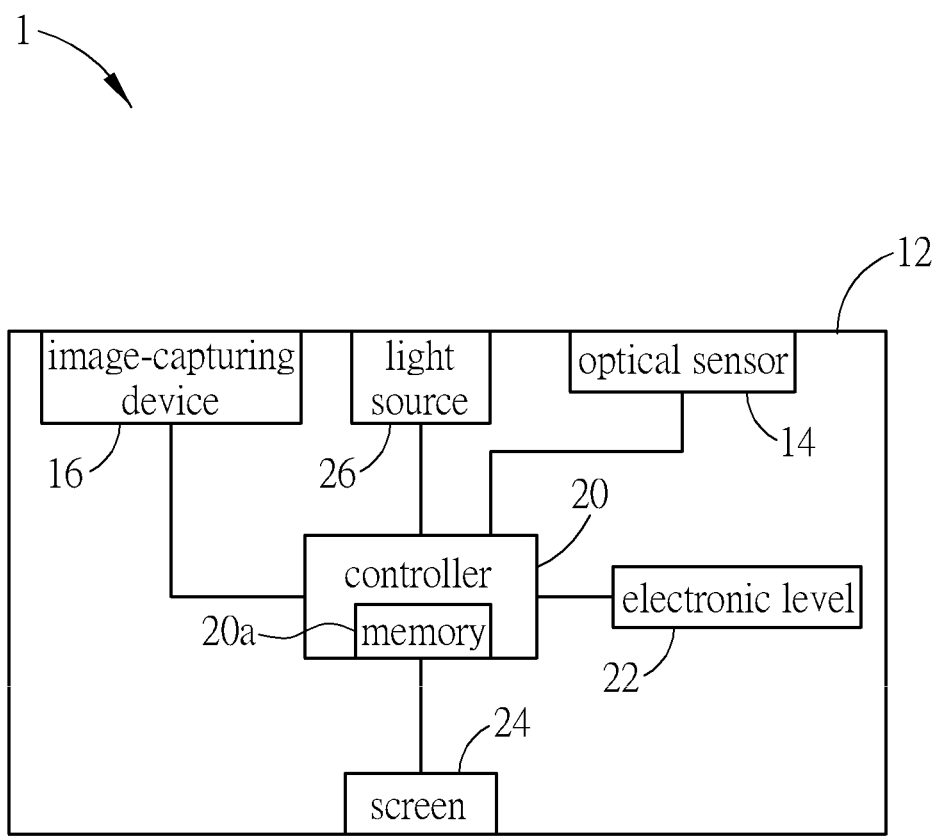
FIG. 2 is a functional block diagram of the optical sensing device in FIG. 1.
Figure 3:
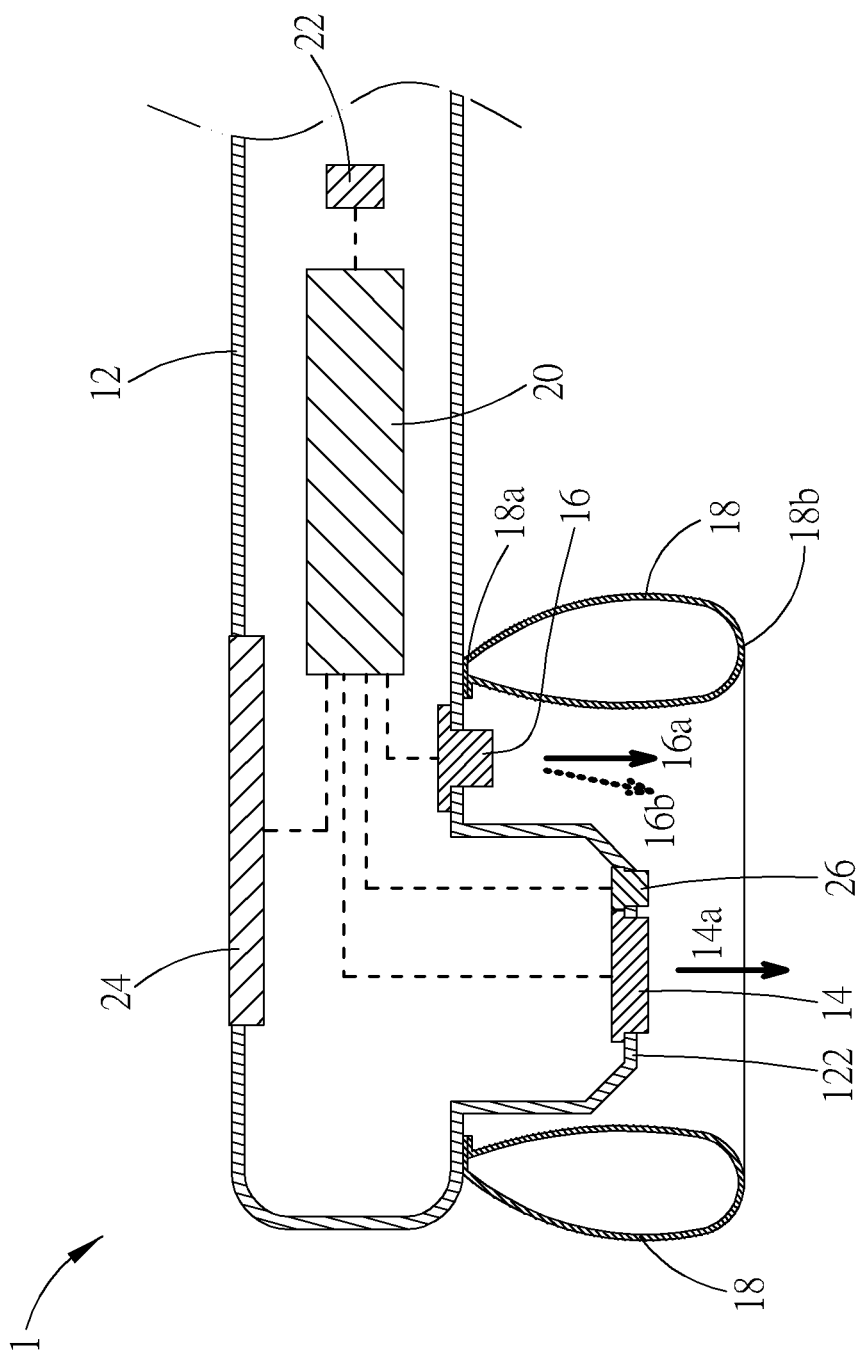
FIG. 3 is a sectional view of the optical sensing device along the line X-X in FIG. 1.

Please refer to FIG. 1 to FIG. 3. An optical sensing device 1 according to an embodiment includes a device casing 12, an optical sensor 14, an image-capturing device 16, a flexible shielding cover 18, and a controller 20; therein, in FIG. 3, the optical sensor 14, the image-capturing device 16, and the controller 20 are represented by solid blocks for drawing simplification. The optical sensor 14 is disposed on the device casing 12 and has a sensing direction 14a (indicated by an arrow in the figures). The optical sensor 14 performs sensing in the sensing direction 14a. The image-capturing device 16 is disposed on the device casing 12 and has a capturing direction 16a (indicated by an arrow in the figures). The image-capturing device 16 performs image capturing in the capturing direction 16a. The flexible shielding cover 18 is disposed on the device casing 12 and encloses the optical sensor 14. The controller 20 is disposed in the device casing 12 and electrically connected to the optical sensor 14 and the image-capturing device 16 (indicated by dashed lines in FIG. 3). The controller 20 has a recording function and in practice can be realized by a circuit board module (e.g. including a circuit board and a processor, memory 20a and other required components which are disposed on the circuit board). The controller 20 can receive optical signals relative to a blood flow through the optical sensor 14 and can receive an image through the image-capturing device 16 and record the received image in the memory 20a. The flexible shielding cover 18 has sufficient flexibility to conform to the surface morphology of an object to be sensed so as to closely fit with the object, for providing a sufficient light shielding effect for the optical sensor 14. The sensing direction 14a and the capturing direction 16a point in the same direction (or the sensing direction 14a and the capturing direction 16a have the same orientation), so that the image-capturing device 16 can capture an image containing at least a portion of the object for providing image information relative to the object. On the other hand, the image-capturing device 16 capturing an image relative to the object to be sensed increases the correlation between the sensing data and the object, i.e. increasing the reference value of the sensing data in the future.

In addition, in the embodiment, as shown by FIG. 3, the optical sensor 14 and the image-capturing device 16 are disposed downward, and the sensing direction 14a and the capturing direction 16a are parallel. However, it is not limited thereto. For example, in an instance, the capturing direction 16b (indicated by a dashed arrow in FIG. 3) of the image-capturing device 16 still faces downward but inclines forward of the optical sensor 14. Therein, the capturing direction 16b and the sensing direction 14a form an acute included angle, but the capturing direction 16b and the sensing direction 14a are still regarded as having the same orientation. In this instance, images captured by the image-capturing device 16 will contain more portions of the object to be sensed, and thereby provide more information relative to the object, i.e. increasing the reusability or reference value of the data.

In the embodiment, the optical sensor 14 can include at least one light source (e.g. green light source, red light source, infrared light source) and an optical detector disposed nearby. The light source emits light, which is reflected by the object to be sensed and then is received by the optical detector. The controller 20 can obtain a sensing result relative to the object by analyzing the light emitted by the light source and the light received by the optical detector, for example but not limited to, in accordance with PPG technology. In practice, the optical sensor 14 can be realized by a common optical sensor based on PPG technology, so the details thereof will not be described in addition. The image-capturing device 16 can include, for example but not limited to, a CCD or CMOS photosensitive device. The flexible shielding cover 18 is a hollow thin shell structure and is made of rubber, so that the flexible shielding cover 18 is so flexible as to easily conform to the surface morphology of the object so as to completely closely fit with the object. On the other hand, as shown by FIG. 3, the hollow thin shell structure can be regarded as a double-layer structure in structure, which includes two side walls. Only the upper and lower ends 18a and 18b of the hollow thin shell structure (i.e. the edges of the side walls of the double-layer structure) are connected in principle. There is gap between the two side walls, so that the hollow thin shell structure as a whole is flexible. The memory 20a can store the captured image, the sensing data (including date, time, optical signals, or information obtained by analyzing the optical signals). Furthermore, the optical sensing device 1 also can include other components (e.g. a power module, a communication module, a connection interface (e.g. but not limited to Bluetooth, WiFi, or USB), and so on).

Please also refer to FIG. 4, which is a sectional view of applying the optical sensing device 1 to sensing an arteriovenous fistula below a skin (therein, the arteriovenous fistula is located at the protruding skin). The arteriovenous fistula itself is not shown in FIG. 4. The flexible shielding cover 18 is obviously protrusive relative to the optical sensor 14 in the sensing direction 14a, so the side wall of the flexible shielding cover 18 can conform to the surface morphology of the skin to bend or buckle before the optical sensor 14 touches the skin. Thereby, the flexible shielding cover 18 can effectively completely closely fit with the skin, so that when the optical sensor 14 senses the arteriovenous fistula, the optical sensor 14 will not be influenced by external light (e.g. ambient light). Furthermore, before, during and after the sensing of the optical sensor 14 to the arteriovenous fistula, the image-capturing device 16 can be used to capture images of the surface morphology of portions of the skin higher than or close to the arteriovenous fistula and record the captured images in memory 20a, by which the correlation between the sensing data and the object is established for future reference.

Furthermore, in the embodiment, the optical sensing device 1 further includes an electronic level 22 disposed on the device casing 12 and electrically connected to the controller 20. The controller 20 receives level data (e.g. tilt angle) from the electronic level 22 and records the received level data in the memory 20a. For example, when the optical sensing device 1 is completely placed on the object to be sensed, the controller 20 records the current level data in the memory 20a, by which the correlation between the sensing data and the level data is established for future reference. In practice, the electronic level 22 can be realized by a six or more-axis digital gyro IC which can be integrated into the circuit board module of the controller 20.

Furthermore, in the embodiment, the optical sensing device 1 further includes a screen 24 (e.g. but not limited to a liquid crystal displaying module) exposed from the device casing 12 and electrically connected to the controller 20. The controller 20 controls the screen 24 to display level information relative to the level data (which can be presented by one or more icons), sensing status, sensing result, time, date, and so on, and even to immediately display an image captured by the image-capturing device 16. Furthermore, in practice, the screen 24 can be realized by a touch display panel, so that the controller 20 also can receive inputs by users through the touch display panel. Furthermore, in practice, the optical sensing device 1 can further includes more keys exposed from the device casing 12 (e.g. disposed near the screen 24) for users to input (e.g. inputting data, control instructions, and so on).

Furthermore, in the embodiment, the optical sensing device 1 further includes a light source 26 disposed on the device casing 12 and electrically connected to the controller 20. The controller 20 controls the light source 26 to project an indication mark in the sensing direction 14a. The indication mark can be a cross, a circle, an arrow, or a polygon, as shown by FIG. 5 to FIG. 6. In practice, the indication mark also can be other figures (including but not limited to letters, numbers, symbols, and so on) or a combination of the above marks, e.g. a cross plus a circle. Furthermore, in practice, the light source 26 can be realized by a light-emitting source (e.g. but not limited to a light-emitting diode) in coordination with a light-guiding rod, an optical fiber, or a lens (used for forming the indication mark, e.g. but not limited to printing light-shielding ink on an end surface of the light-guiding rod or optical fiber or on a surface of the lens to form a pattern matching the indicator mark). The indication mark can be projected onto the object to be sensed (e.g. the skin above the arteriovenous fistula) or near the object, which can provide a reference for the user to move the optical sensing device 1, so that the optical sensing device 1 can be moved toward the object more precisely. In the embodiment, the light source 26 is disposed adjacent to the optical sensor 14 to make the projected indication mark closer to the object, so that the user can precisely move the optical sensing device 1. Furthermore, in practice, the projection direction of the light source 26 can slightly incline to the sensing direction 14*a* so that the projected indication mark can be much closer to the object.

Figure 4:
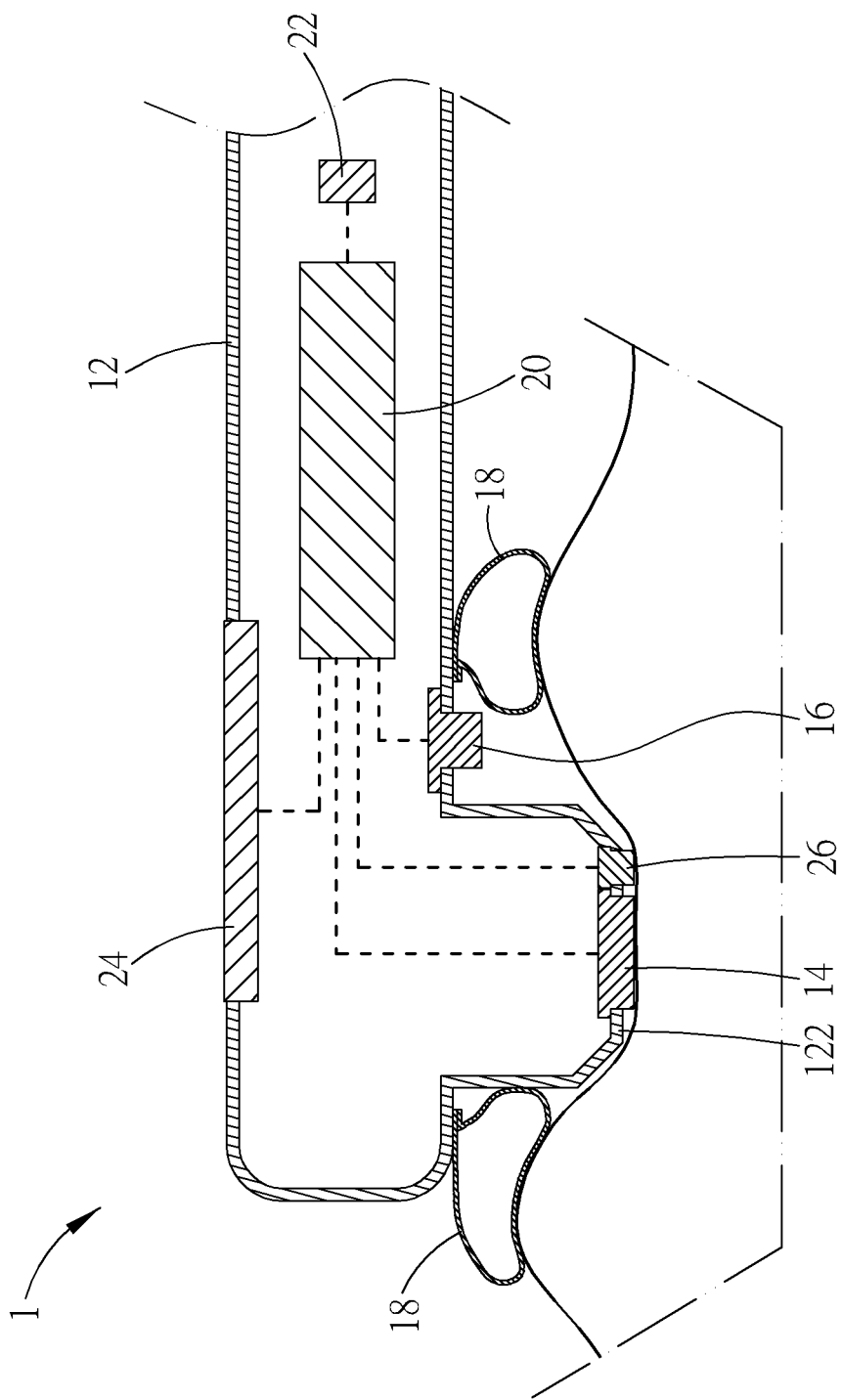
FIG. 4 is a sectional view of applying the optical sensing device in FIG. 3 to sensing an arteriovenous fistula below a skin.

As shown by FIG. 1, FIG. 3 and FIG. 4, in the embodiment, the device casing 12 further has a protruding platform 122 protruding from the device casing 12 in the sensing direction 14*a*. The optical sensor 14 is disposed on the protruding platform 122, which can reduce structural interference of the optical sensing device 1 with the object to be sensed (and other structures near the object) so as to make the optical sensor 14 be closer to or completely closely fit with the object. In the embodiment, the light source 26 is also disposed on the protruding platform 122, which makes it easier to project the indication mark close to the object. Furthermore, the image-capturing device 16 is disposed on the device casing 12 adjacent to the protruding platform 122. The flexible shielding cover 18 encloses the image-capturing device 16. This structural configuration can prevent the flexible shielding cover 18 from shielding the image-capturing device 16 from capturing images of the object. This structural configuration is also suitable for the image-capturing device 16 to capture images for confirming or recording the actual position of the optical sensing device 1 (or the protruding platform 122) relative to the object (e.g. in coordination with other light source that temporarily provides light required for the image capturing), after the flexible shielding cover 18 completely closely fit with the object. Furthermore, the flexible shielding cover 18 is obviously protrusive relative to the protruding platform 122 in the sensing direction 14*a*, also relative to the optical sensor 14, so the flexible shielding cover 18 can effectively completely closely fit with the skin before the optical sensor 14 touches the skin.

Figure 9:
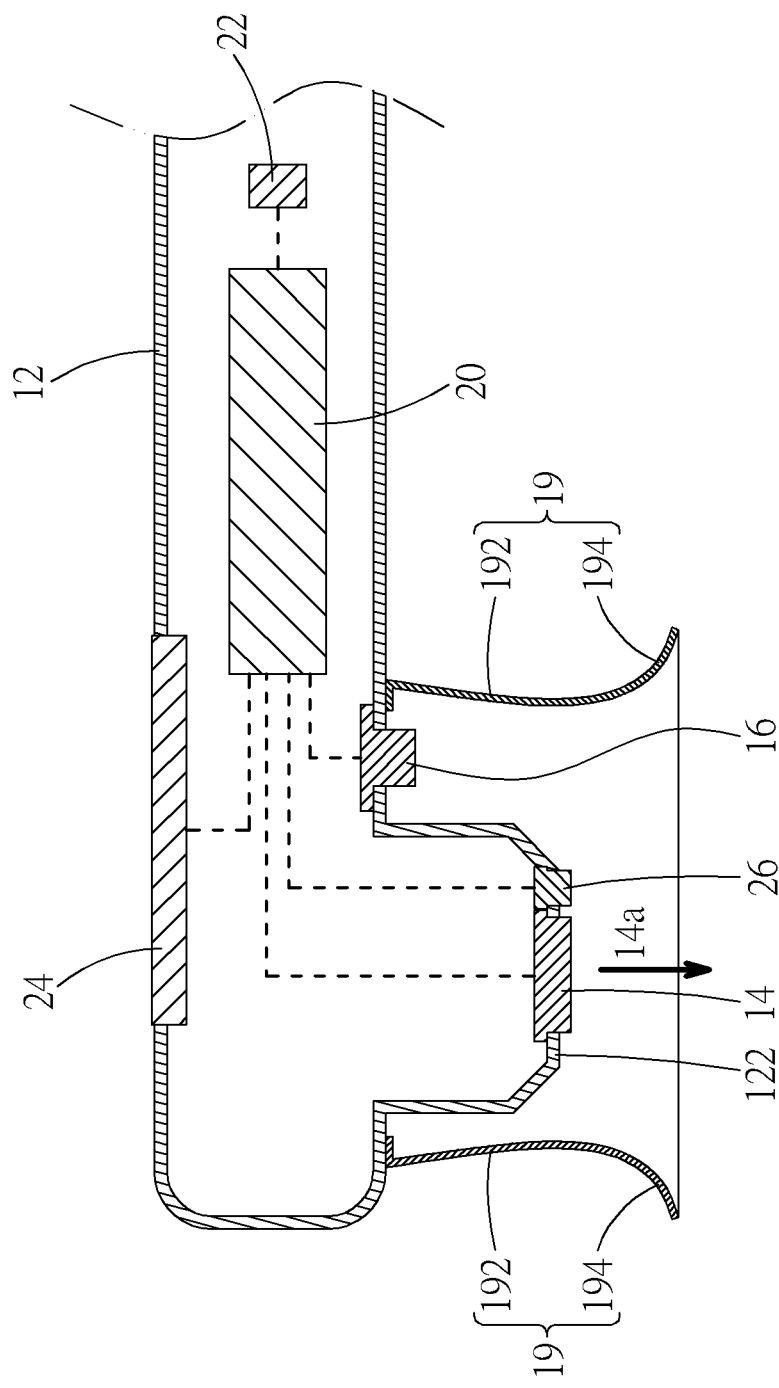
FIG. 9 is a sectional view of an optical sensing device according to another embodiment.

In addition, in the embodiment, the flexible shielding cover 18 as a whole has a cross-section profile in the sensing direction 14*a* (i.e. the cross-section profile is on a reference plane perpendicular to the sensing direction 14*a*). The cross-section profile is a rectangle for matching the profile of the protruding platform 122; however, in practice, the cross-section profile also can be a circle, an ellipse or other polygons. Furthermore, in practice, the flexible shielding cover 18 can be designed to be exchangeable (e.g. detachably attached to the device casing 12), so that the flexible shielding cover 18 can be replaced with another one with different structural profile for matching different objects to be sensed (e.g. the protruding skin above the arteriovenous fistula has different morphology). In addition, in practice, the flexible shielding cover 18 also can be a non-hollow thin shell structure. As shown by FIG. 9, another flexible shielding cover 19 replaces the flexible shielding cover 18 to be disposed on the device casing 12. The flexible shielding cover 19 includes a shroud portion 192 and a ringed lip portion 194. The shroud portion 192 is disposed on the device casing 12. The ringed lip portion 194 extends outward from the shroud portion 192. The flexible shielding cover 19 can be realized by a thin shell structure made of rubber, which can easily provide sufficient flexibility to conform to the surface morphology of the object to be sensed so as to closely fit with the object. Therein, the outwardly extending ringed lip portion 194 can effectively completely closely fit with the object, so that the flexible shielding cover 19 also can provide the same light shielding effect as the flexible shielding cover 18 does. For other descriptions about the flexible shielding cover 19, please refer to the relevant descriptions of the flexible shielding cover 18 and variants thereof (about the profile of the flexible shielding cover 18, the disposition relationship between the flexible shielding cover 18 and other structures, and so on), which will not be described in addition.

The usage of the optical sensing device 1 can be implemented by the following steps; however, it is not limited thereto in practice. First, a subject's arm needs to be laid flat. The optical sensing device 1 needs to be turned on by a user (e.g. the subject). The optical sensor 14, the image-capturing device 16, the electronic level 22, and the light source 26 are also set to be on. Then the user needs to make the indication mark projected by the light source 26 on or near a test spot (or a smaller area, i.e. the object to be sensed) of the arm. In practice, for example, if the optical sensing device 1 is used for sensing the status of a blood flow in an arteriovenous fistula for renal dialysis, the selection of the test spot to be sensed should be set away from the upper and lower injection sites, so as to avoid the influence of turbulence herein on the sensing.

Afterwards, the user needs to move the optical sensing device 1 so as to align the optical sensor 14 with the test spot and move the optical sensor 14 to the test spot. At the same time, the flexible shielding cover 18 needs to completely closely fit with the skin near the test spot, for preventing external light from entering the flexible shielding cover 18 to influence the sensing result of the optical sensor 14. In practice, a patient probably wrapped cling film on the skin above the arteriovenous fistula for protecting anesthetic coating area. Even for this case, the flexible shielding cover 18 still can effectively completely closely fit with the skin with the cling film thereon. Furthermore, at the moment, the screen 24 on the optical sensing device 1 can display the current status of the fitting angle (e.g. displaying current level data generated by the electronic level 22).

The optical sensor 14 continuously senses the blood flow of the arteriovenous fistula. After the controller 20 determines that the optical signals relative to the blood flow in the arteriovenous fistula are stable (e.g. keeping stable for a short period of time), the controller 20 calculates a blood flow magnitude according to the optical signals and records the blood flow magnitude in the memory. The controller 20 also records current level data, an image captured by the image-capturing device 16 (which can be captured before the flexible shielding cover 18 completely closely fits with the skin, or when the indication mark is projected on the test spot), time, date, and so on (in the memory 20*a*). The above operation of the controller 20 can be automatically executed through firmware recorded in the controller 20. In principle, the user just needs to turn on the optical sensing device 1 and move the optical sensing device 1 to align with the test spot, or after the alignment with the test spot is completed, the user needs to trigger the optical sensor 14 to start sensing. The entire operation on the optical sensing device 1 is simple and no professional knowledge is required, which is quite suitable for patient self-testing, saving time for patients to rush to professional medical institutions. In practice, as shown by FIG. 10, each data recorded in the memory 20*a* by the controller 20 may include an identification code (e.g. setting corresponding identification codes for different patients), a sensing time (e.g. obtained by accessing system time of the optical sensing device 1 after the optical signals are stable), a blood oxygen saturation (SPO2) (e.g. inputted by user), a systolic blood pressure (e.g. inputted by user), a diastolic blood pressure (e.g. inputted by user), a blood flow magnitude (calculated by the controller 20 according to the optical signals), a signal acquisition duration (e.g. calculated by the controller 20 according to the system time), an image (i.e. the captured image, which is recorded by a file name and can show the surface morphology of the test spot, e.g. is there a foreign object on the skin, a skin condition, e.g. skin color, hair and so on), a level status (e.g. according to the level data), an equipment number (e.g. the predetermined serial number of the optical sensing device 1), a firmware version, remarks (which can be added by users, for example, the skin of the patient sensing area is covered with cling film) and so on. These data can increase the correlation between the blood flow magnitude and other datum items (e.g. blood oxygen saturation, systolic blood pressure, diastolic blood pressure and so on) (e.g. the relationship between the blood flow magnitude and the blood pressures), and also can increase the reusability or reference value of the data. The above values inputted by users can be performed, for example but not limited to, through a screen having a touch function, or through keys provided on the optical sensing device 1 in coordination with the screen 24. Furthermore, in practice, the optical sensing device 1 can transfer the stored data in the memory 20a to an external electronic device (e.g. computer host) through a communication module, for data storage, data collection, further analysis, or other data processing.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An optical sensing device, comprising:
   a device casing;
   an optical sensor, disposed on the device casing and having a sensing direction, the optical sensor performing sensing in the sensing direction;
   an image-capturing device, disposed on the device casing and having a capturing direction, the sensing direction and the capturing direction pointing in the same direction; and
   a flexible shielding cover, disposed on the device casing and enclosing the optical sensor and the image-capturing device.

2. The optical sensing device according to claim 1, further comprising a light source, disposed on the device casing, wherein the light source projects an indication mark in the sensing direction, and the indication mark is one of a cross, a circle, an arrow, and a polygon.

3. The optical sensing device according to claim 1, wherein the flexible shielding cover is a hollow thin shell structure.

4. The optical sensing device according to claim 1, further comprising a light source, disposed on the device casing, wherein the light source projects an indication mark in the sensing direction, the device casing has a protruding platform, the optical sensor and the light source are disposed on the protruding platform, the light source is adjacent to the optical sensor, and the image-capturing device is adjacent to the protruding platform.

5. The optical sensing device according to claim 1, wherein the flexible shielding cover comprises a shroud portion and a ringed lip portion, the shroud portion is disposed on the device casing, the ringed lip portion protrudes outward from the shroud portion, the flexible shielding cover has a cross-section profile in the sensing direction, and the cross-section profile is one of a circle, an ellipse, and a polygon.

6. The optical sensing device according to claim 1, further comprising a controller, disposed in the device casing and electrically connected to the optical sensor and the image-capturing device, wherein the controller has a memory, and the controller receives optical signals relative to a blood flow through the optical sensor, receives an image through the image-capturing device and records the received image in the memory.

7. The optical sensing device according to claim 6, further comprising an electronic level, disposed on the device casing, wherein the controller is electrically connected to the electronic level, and the controller receives level data from the electronic level and records the received level data in the memory.

8. The optical sensing device according to claim 7, further comprising a screen, exposed from the device casing, wherein the controller is electrically connected to the screen, and the controller controls the screen to display level information relative to the level data.

9. The optical sensing device according to claim 6, wherein the controller calculates a blood flow magnitude according to the received optical signals and records a sensing time or a signal acquisition duration relative to the received optical signals in the memory.

10. The optical sensing device according to claim 6, wherein the controller receives a value relative to a blood oxygen saturation, a systolic blood pressure, or a diastolic blood pressure from outside and records the received value in the memory.

* * * * *